(12) United States Patent
Borowczak et al.

(10) Patent No.: US 6,536,289 B2
(45) Date of Patent: Mar. 25, 2003

(54) AUTOMATED SAMPLE TESTER

(75) Inventors: Marc Borowczak, North Canton, OH (US); Cristina Marie Gschnell, Canal Fulton, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/932,179

(22) Filed: Aug. 17, 2001

(65) Prior Publication Data
US 2003/0033896 A1 Feb. 20, 2003

(51) Int. Cl.$^7$ .................................................. G01N 3/32
(52) U.S. Cl. ................................................ 73/809; 73/856
(58) Field of Search ......................... 73/866, 809, 819, 73/856, 855

(56) References Cited

U.S. PATENT DOCUMENTS

| 2,419,711 A | * | 4/1947 | Dillon ........................ 73/859 |
| 3,491,586 A | * | 1/1970 | Branger ...................... 374/47 |
| 3,983,745 A | * | 10/1976 | Juusola ....................... 73/789 |
| 4,606,230 A | * | 8/1986 | Scott et al. .................. 73/856 |
| 4,813,287 A | * | 3/1989 | Walzel et al. ................ 73/835 |
| 4,876,658 A | * | 10/1989 | Hass .......................... 364/550 |
| 5,465,610 A | * | 11/1995 | Loisel ........................ 73/60.11 |
| 5,493,511 A | * | 2/1996 | Wincheski et al. ......... 364/508 |
| 5,607,861 A | * | 3/1997 | Komatsu et al. ............ 436/50 |
| 5,883,311 A | * | 3/1999 | Hettiarachchi et al. ...... 73/799 |
| 5,918,284 A | * | 6/1999 | Blanch et al. ............... 73/827 |
| 6,079,284 A | * | 6/2000 | Yamamoto et al. ........ 73/865.8 |
| 6,089,107 A | * | 7/2000 | Canella et al. ............. 73/865.8 |
| 6,170,980 B1 | * | 1/2001 | Martin ....................... 366/191 |
| 6,257,079 B1 | * | 7/2001 | Mueller ...................... 73/866 |

FOREIGN PATENT DOCUMENTS

JP 355156831 A * 12/1980 ............ G01N/3/34

* cited by examiner

Primary Examiner—Hezron Williams
Assistant Examiner—C D Garber
(74) Attorney, Agent, or Firm—David E Wheeler; Richard B O'Planick

(57) ABSTRACT

An apparatus for testing a plurality of samples comprises a carousel, means for indexing the movement of the carousel, an environmental chamber, and means for positioning the sample for viewing and measuring the results of the testing. The environmental chamber makes possible testing at elevated or reduced temperatures, and testing in a variety of atmospheres. The sample positioning means and the viewing means are automated.

15 Claims, 7 Drawing Sheets

AUTOMATED SAMPLE TESTER

FIELD OF THE INVENTION

The invention relates to a testing apparatus which automatically handles a plurality of samples

BACKGROUND OF THE INVENTION

In the testing of the durability of rubber compounds, one test that is used is a dynamic flexing test. In the dynamic flexing test, the rubber being tested is formed into a thin sample and two ends of the sample are anchored in opposing sample holders. The sample holders are fixed into an apparatus which is capable of stretching the sample at 10 cycles per second or more. Prior to flexing the sample, a small cut is placed in the edge of the sample to initiate cracking of the rubber, and the fracture resistance of the rubber comprising the sample is measured by the propagation rate of a crack resulting from the dynamic flexing.

The length of the crack, and the path of the crack provide information to the engineer which can be used to make predictions as to the performance of the rubber when used as a component of an elastomeric product.

In the prior art, measurements were made manually and a written description of the cut path was provided. In some embodiments of the test, pictures were taken of the sample after completion of the flex testing.

In variations of the test, the rubber sample may be subjected to aging, i.e. subjected to oxidizing or reducing atmosphere and heated, to get additional data on the aging properties of the rubber sample.

The testing of individual samples, or a small number of samples is laborious and time-consuming. There is a need in the art for an apparatus and method whereby a large number of samples can be tested simultaneously and the results can be determined substantially automatically.

SUMMARY OF THE INVENTION

The invention relates to an apparatus for automatically testing multiple samples comprising a carousel having a plurality of stations for holding samples to be tested. Sample holding means associated with the carousel are adapted to retain samples during static or dynamic testing of the samples and to release the samples when measurements are made.

In the illustrated embodiment, a vacuum device associated with the carousel is used to remove a sample from the sample holding means, and a measuring device associated with the carousel is used for evaluating a sample when a sample is withdrawn from the sample holding means by the vacuum device.

In the illustrated embodiment, the sample holding means and vacuum device are contained within an environmental chamber and the measuring device is an imaging device outside the environmental chamber.

The carousel has an upper part and a lower part and the sample holding means has a first portion associated with the upper part of the carousel and a second portion associated with the lower part of the carousel. The lower part and upper part of the carousel are moveable relative to one another, i.e. the upper portion and the lower portion of the carousel are actuated to move toward and away from each other while sample holding means in the upper portion and lower portion remain aligned.

The upper portion and the lower portion of the carousel are mounted on a spindle, and actuating means is provided for advancing the carousel in increments corresponding to sample holding means in the carousel. In the illustrated embodiment, the lower portion and upper portion of the carousel are actuated ten times per second to provide dynamic flexing of rubber samples.

The environmental chamber has means for controlling atmosphere and temperature.

In the illustrated embodiment of the invention, the measuring means is a digital imaging device.

A method for automating the testing of a sample using the apparatus of the invention is also provided.

BRIEF DESCRIPTION OF THE DRAWINGS

The invention will be described by way of example and with reference to the accompanying drawings in which.

DETAILED DESCRIPTION OF THE INVENTION

Figure 1:
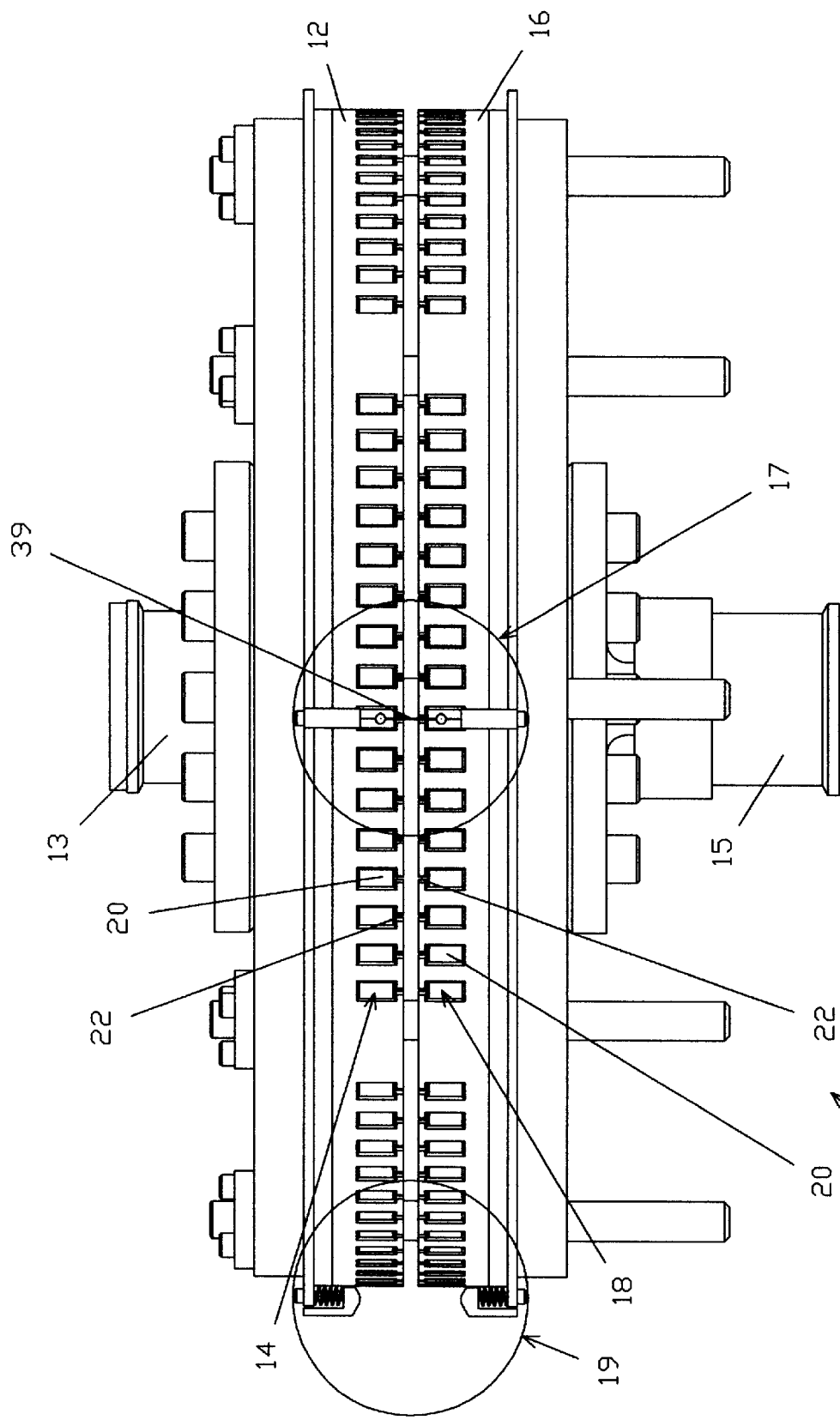
FIG. 1 illustrates a carousel with a multiplicity of sample holders of the invention.
Figure 1A:
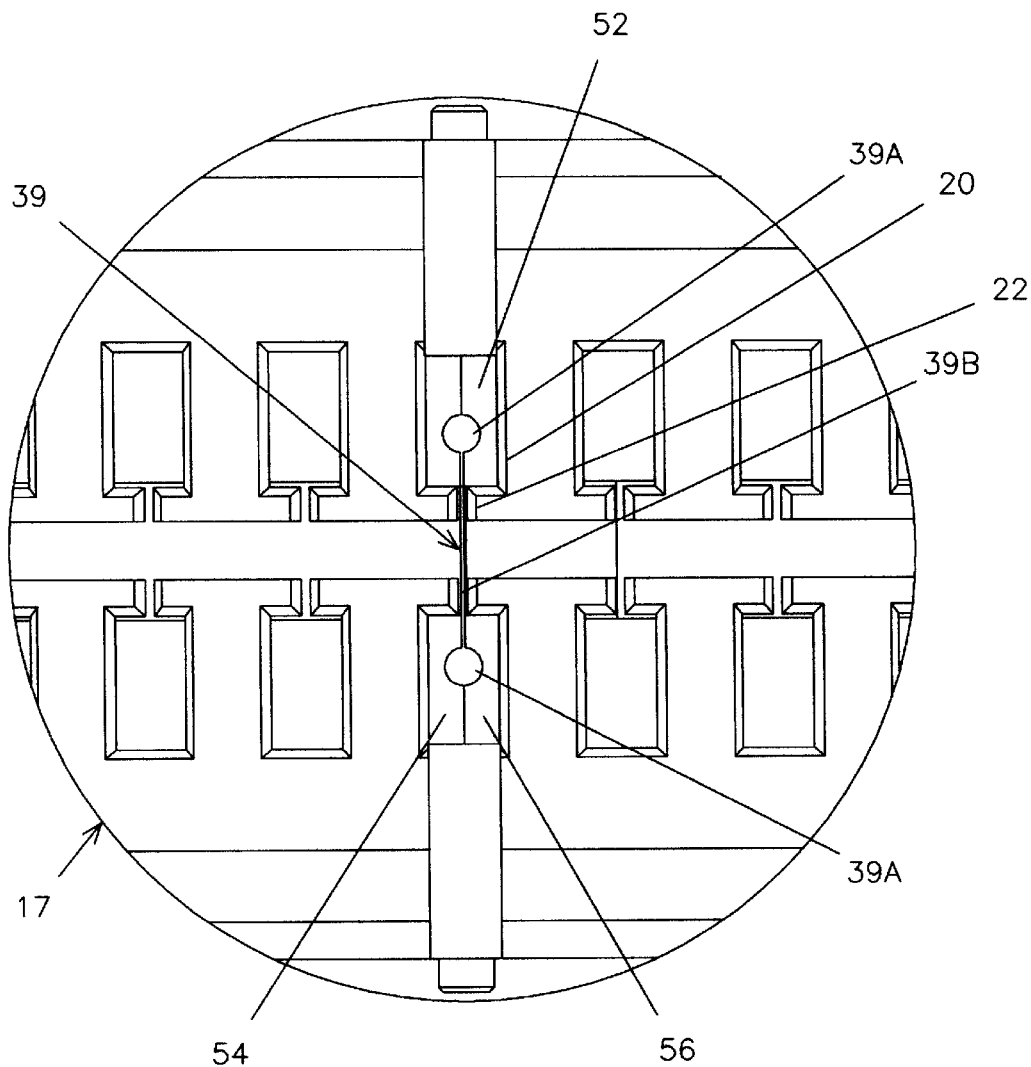
FIG 1A is an enlargement of a sample positioned in a carousel of FIG. 1.
Figure 1B:
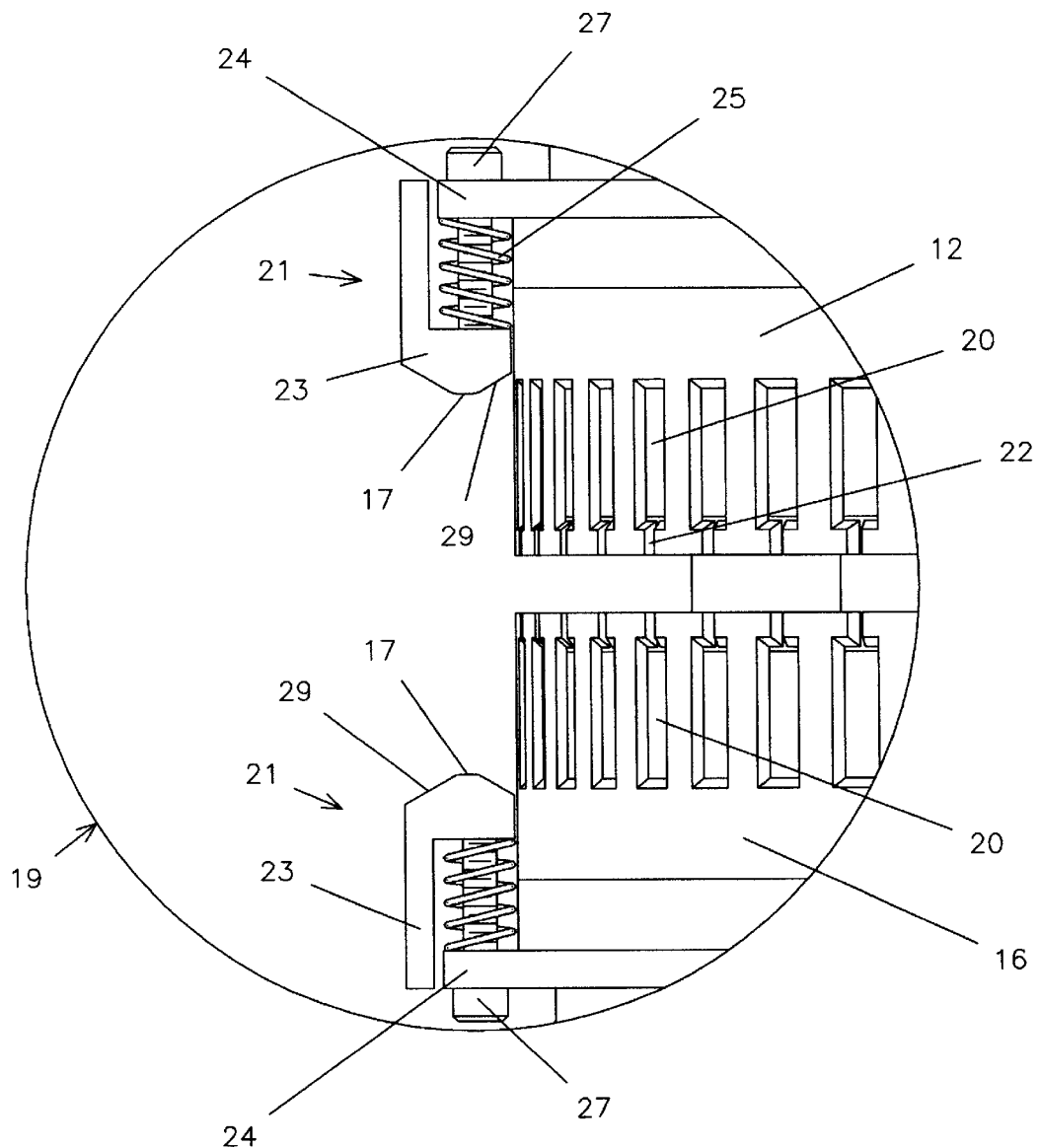
FIG. 1B is an enlargement of a spring-loaded sample stopper.

With reference now to FIGS. 1, 1A and 1B in accordance with the present invention, a carousel 10 is provided which comprises an upper sample plate 12, and a lower sample plate 16. The carousel has an upper collar 13 and a lower collar 15 for mounting the carousel 10 on to a spindle. Upper sample plate 12 and lower sample plate 16 are designed to hold a plurality of sample holders 14, 18 in alignment with one another. Sample holders 14, 18 each comprise a chamber 20 and a neck 22. When a sample 39 is prepared for use in the apparatus, an enlarged portion of the sample 39A (FIG. 1A) is designed to be held within the opposed chambers 20, whereas a thinner portion of the sample 39B fits into neck 22 of sample holders 14, 18.

When a sample is being tested, the apparatus is actuated so that at least one of sample plate 12 and sample plate 16 moves back and forth so that the gap between sample plate 12 and sample plate 16 is increased and decreased at a rate of 2 to 15 cycles per second (CPS). This movement of the upper sample plate 12 and lower sample plate 16 relative to each other stretches the sample and allows the sample to contract at a rate defined by the relative motion of the two plates.

In the illustrated embodiment, a hydraulic actuator 47 (FIG. 4) is used to activate the sample plates 12,16. Such an actuator is currently in use on commercial dynamic flex testing equipment such as the MTS-831.

As in the prior art test for dynamic crack growth, a crack is initiated in the sample by a small cut before the test commences, and the crack growth and the path of the crack are examined in an effort to characterize the physical properties of the rubber contained within the sample.

The cyclic movement of the sampling plates may be controlled to simulate, as closely as possible, the conditions likely to be encountered by the material of the sample in use in a product. For example, the driving signals for the cycling mode may comprise sine waves, square waves or other signals that may be considered appropriate. In a tire, for example, it is believed that none of the components in a tire undergo sinusoidal conditions during tire rotation, and the more abrupt cycling conditions of a pulse wave are considered more appropriate for testing tire materials. Other suitable signals for other applications will be apparent to those skilled in the art.

With reference now to FIG. 1A, optionally the samples 39 may be prepared with brass ends 52. In the illustrated embodiment, brass ends 52 comprise two pieces 54, 56 which clamp the ends 39A of the samples and are held together with mechanical means such as screws.

The brass ends 52 provide rigidity for easy insertion of the sample 39 into cavity 20 of the sample holders 14, 18. The brass ends 52 also provide a non-porous, uniform surface for attachment of vacuum cups (described below), and a uniform consistent coefficient of friction that makes possible the useful determination of the force necessary to remove a sample from the sample holder.

With reference now to FIG. 1B, in the illustrated embodiment a spring-loaded restrictor 21 is used to retain the brass ends 52 (FIG. 1A) of a sample in a sample cavity 20. The restrictor 21 comprises a hood 23 which is movably connected to a bolt 27. A spring 25 is interposed between hood 23 and a flange 24, which receives bolt 27. Spring 25 tends to hold hood 23 in a position that extends over the edge of a brass end 52 when a sample 39 having brass ends is held in cavities 20.

When a sample 39 having brass ends 52 is inserted into carrousel 10, sloped sides 29 of hood 23 permits sliding of brass ends 52 over hood 23 while hood 23 compresses spring 25. When a sample 39 is in place, spring 25 pushes hood 23 away from flange 24 so that end 17 of hood 23 extends beyond the edge of brass ends 52.

When a sample is removed from a cavity 20, the brass ends 52 presses against sloped sides 29 of hood 23, causing hood 23 to be pushed aside, permitting removal of a sample.

In the illustrated embodiment, end 17 of hood 23 extends about 0.016 inch past the edge of a brass end 52 when it is in a sample cavity 20. Sloped sides 29 have about a 30° angle with respect to the plane of sample plates 12 and 16. Those skilled in the art will recognize that other physical parameters may be chosen that will be suitable for the stated purpose.

Figure 2:
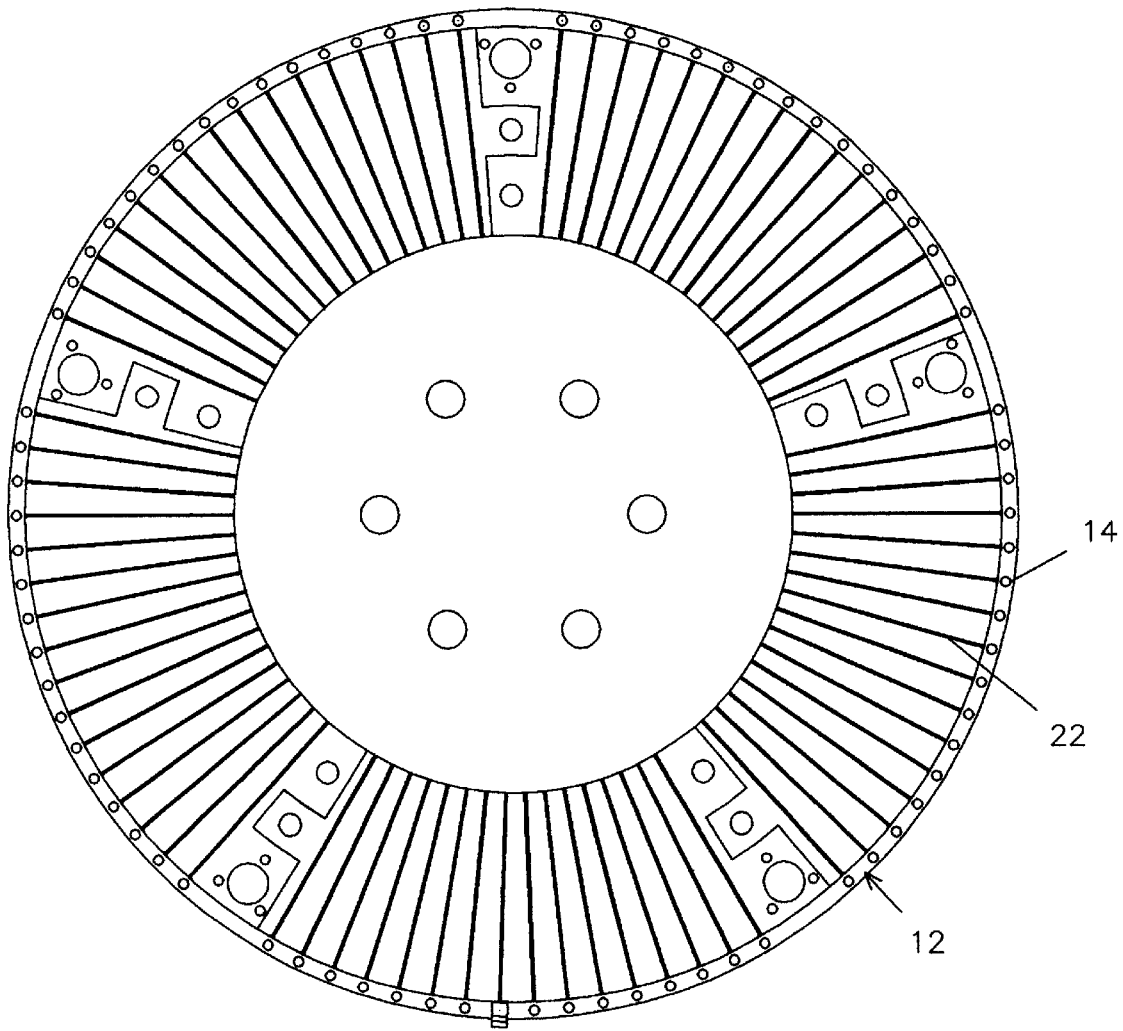
FIG. 2 illustrates a cut-away top view of the lower part of the carousel illustrated in FIG. 1.

With reference now to FIG. 2, a cross-section of the carousel illustrated in FIG. 1 is shown which illustrates the top of sample plate 16, showing a top view of the necks 22 of the sample holders 14. In the illustrated embodiment, the apparatus is designed to hold about 80 samples. Those skilled in the art will recognize that larger or smaller devices can be designed holding more or fewer samples, depending on the perceived needs for the testing made possible using the apparatus.

In addition to the cyclic movement described with reference to FIG. 1, the apparatus is designed with indexing means to permit incremental rotational movement of the carousel so that sample plates 12,16 can be incrementally positioned so that each of the samples, which are subjected to testing can be moved to a specific position in the apparatus. That is, the carousel can be rotated so that each position on the 360° circumference of the carousel can be passed by a specified point in the testing apparatus.

Figure 4:
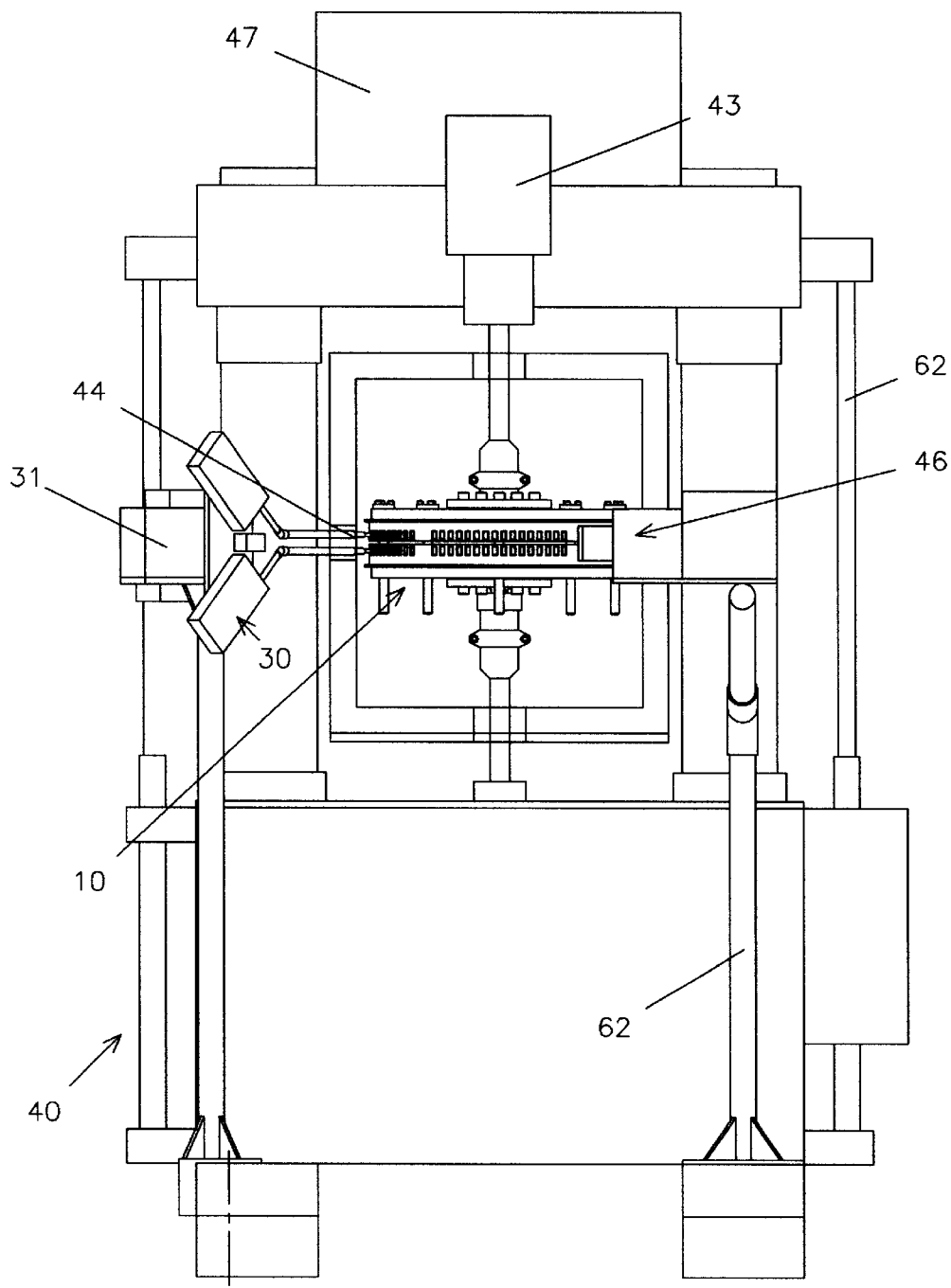
FIG. 4 illustrates a frontal view of the environmental chamber of the apparatus of the invention.

In the illustrated embodiment, a Parker-Hannifin stepper motor/gear box/chain drive combination 43 is utilized to provide incremental rotation of the sample carousel (FIG. 4). A similar arrangement is used in autoanalyzers known in the art. Those skilled in the art will be able to devise other mechanical means for indexing the samples in the apparatus.

Each sample is sequentially removed from the carousel by a sample positioning means, which in the illustrated embodiment is a vacuum apparatus, which is mounted to a linear actuator driven by a servo-motor.

Figure 3:
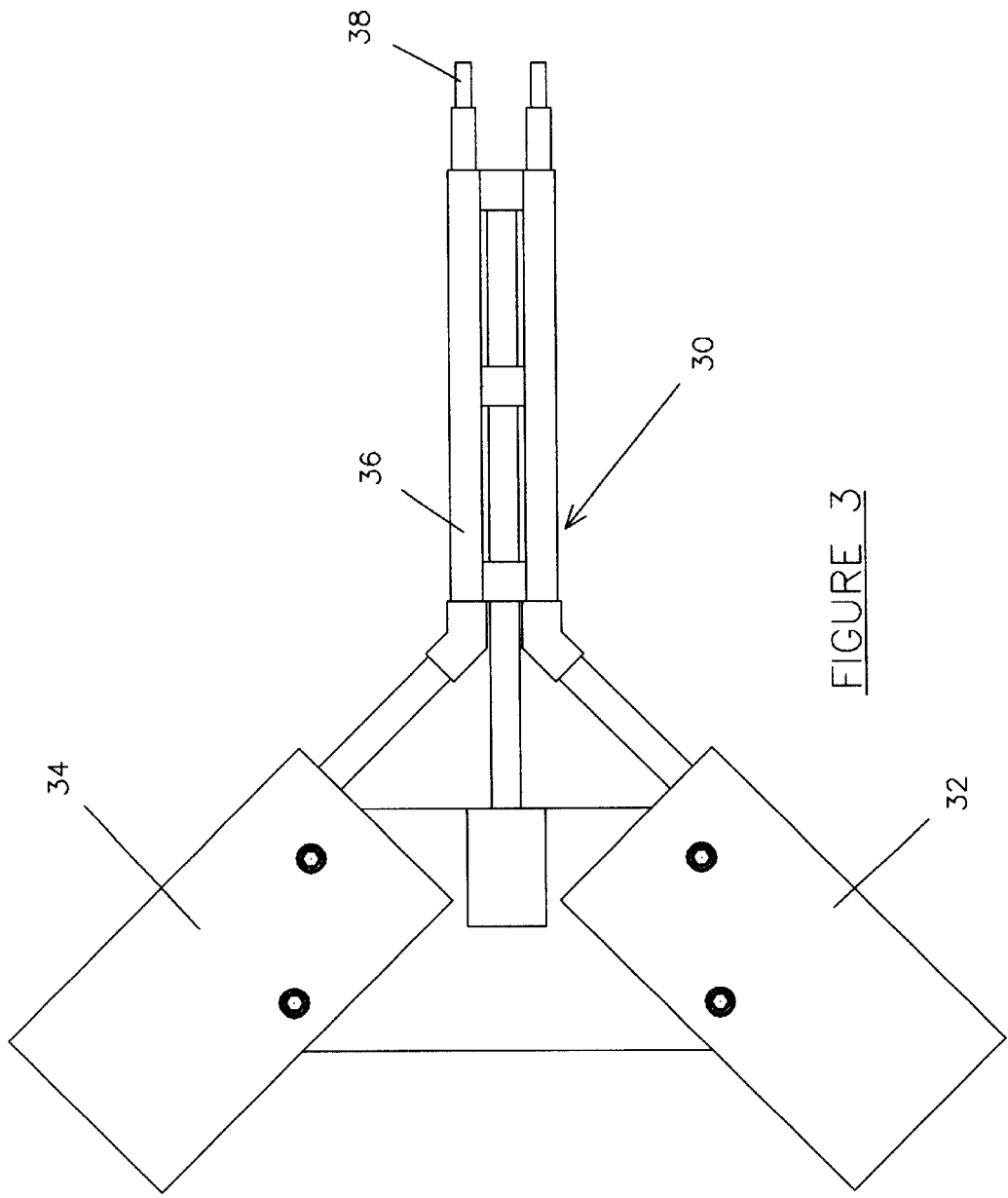
FIG. 3 illustrates a vacuum assembly used in the apparatus of the invention for extracting a sample from the sample holder.

With reference now to FIG. 3, a vacuum apparatus 30 is illustrated which is located at a specific point in the apparatus such that when a sample is rotated to the position of vacuum apparatus 30, the vacuum apparatus can be used to withdraw a sample 39 from the sample holders 14, 18. Vacuum apparatus 30, in the illustrated embodiment, comprises vacuum generators 32, 34 and vacuum tubing 36, which is connected to mini bellow vacuum cups 38. Vacuum cups 38 are brought into proximity to sample 39, and the vacuum created by vacuum apparatus 30 holds sample 39 while the servo-motor withdraws vacuum system 30 pulling sample 39 out of sample holders 14, 18 so that sample 39 can be viewed.

Figure 5:
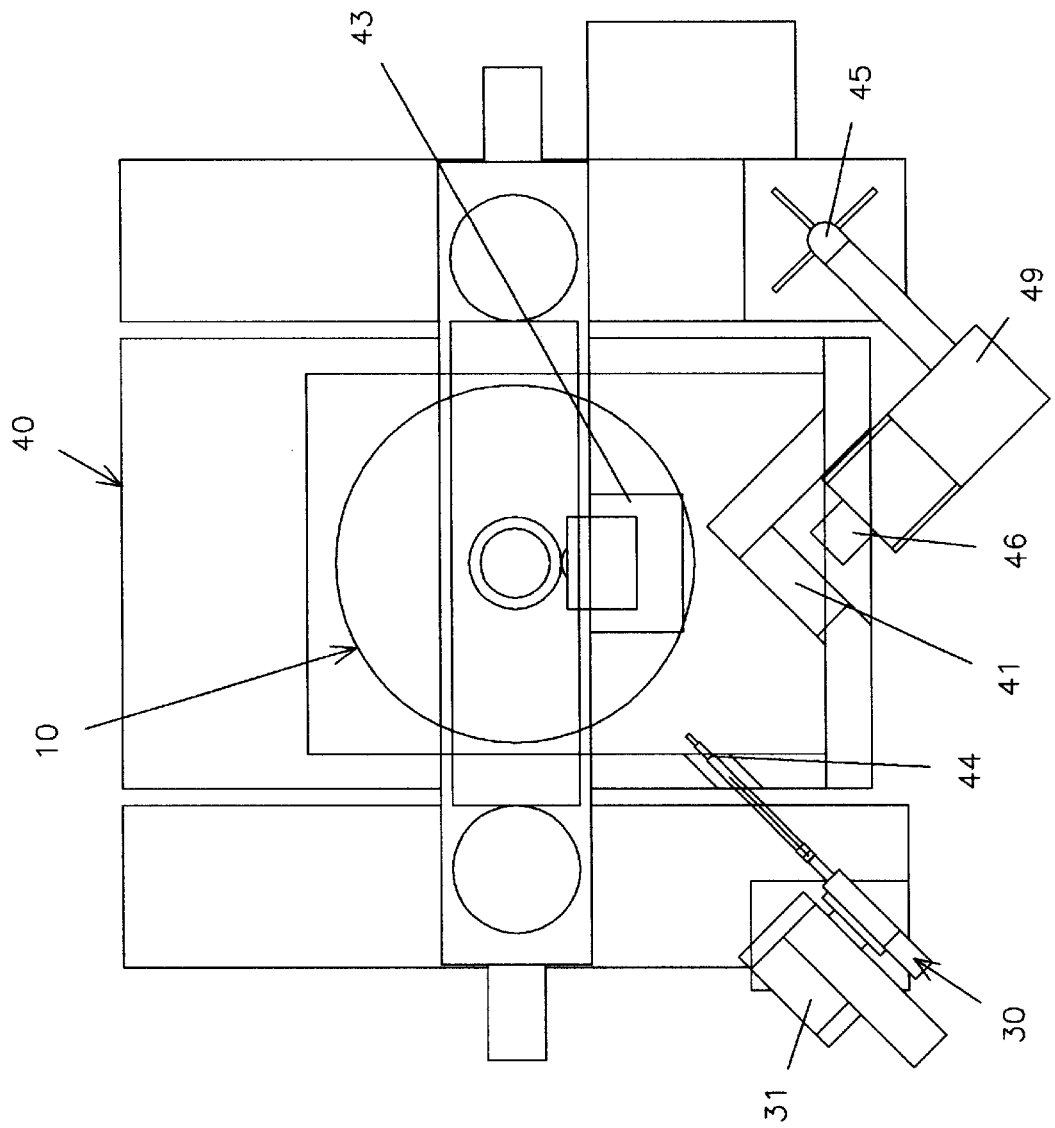
FIG. 5 illustrates a top view of the environmental chamber of the apparatus of the invention.

With reference now to FIGS. 4 and 5, in an environmental chamber 40 of the apparatus, a port 44 is provided for vacuum apparatus 30 which is at a 90° angle to port which is used as a viewing port. When a sample 39 is withdrawn from sample holders 14, 18 by vacuum apparatus 30, it is pulled into the field of vision of a means for measuring the results, for example, a digital camera 49, which may be located at port 46. The digital camera 49 may be used to recreate an image of the sample as well as to collect digital data regarding the length of a crack as well as the path of a crack which is formed in the sample during the dynamic fracture testing.

Vacuum system 30, using the linear servo-motor 31 is moved back and forth with respect to environmental chamber 40 as samples 39 are removed from sample holders 14,18, causing vacuum tubing 36 to retract through port 44. The servo-motor can be calibrated to move an exact distance toward and away from samples 39. Optionally, to insure that sample 39 is precisely located in the apparatus, so that when vacuum system 30 is actuated, bellows vacuum caps 38 are in position to lock onto a sample, spring-loading device 17 (FIG. 1B) can be included in sample plates 12, 16 to hold a sample 39 in place.

The spring-loading device is strong enough to provide some resistance to the sample, but not so strong as to prevent movement of the sample by vacuum system 30.

With reference again to FIG. 1B, in the illustrated embodiment, spring-loaded stoppers are mechanically attached to the upper and lower portions of the carousel. The stoppers are aligned in front of each sample to prevent sample movement out of the sample holders 14, 18 radially during cyclic testing and indexing.

Those skilled in the art will recognize that alternative methods of holding the sample in position can be used.

Although, in the illustrated embodiment, the measurements are obtained using a digital camera 49, and the results are recorded in real time and stored in a data base, those skilled in the art will recognize that other means of measuring the sample can be used.

In the illustrated embodiment, port 46 is covered with heat resistant glass 41 in one, two or three panes, and digital camera 49 is located outside environmental chamber 40. When a plurality of glass panes is used, such panes may be separated by a vacuum.

In the illustrated embodiments digital camera 49 is attached to shaft 45 which can be rotated on its axis so that digital camera 49 can be moved away from the door of environmental chamber 40 when samples 39 are inserted or removed from carousel 10. The digital camera is preferably locked in place when it is used. Those skilled in the art will recognize that digital cameral 49 can be fixed to a wall of environmental chamber 40 which is remote from the door.

The motion and visual systems of the test apparatus are coordinated using a microprocessor. The vision analysis of crack length and failure mode is done using a personal computer. The personal computer software will communicate failure of a sample to the motion microprocessor. This intelligence will allow failed samples to be bypassed on further cyclic crack length analysis.

Since the apparatus is automated, testing may be conducted continuously around the clock.

Environmental chamber 40 is an enclosed, sealable structure which may contain heating elements or otherwise be filled with a super heated atmosphere. Alternatively, cooling means, such as liquid nitrogen, may be used to reduce the temperature of the atmosphere within environmental chamber 40. In addition, ports may be provided for injecting gases appropriate for creating an aging or inert environment, depending on the testing desired. Examples of gases that may be used to test the aging properties of a sample include oxidizing or reducing gases such as $O_3$, $Cl_2$, $Br_2$, and $F_2$. $N_2$ is generally considered to be an inert atmosphere for most rubber testing. Those skilled in the art will recognize other suitable atmospheres for testing aging properties may be used, and any atmosphere that is believed to provide useful physical data can be used in the environmental chamber during the testing.

The environmental chamber may include $O_2$ monitors and other sensors that can be used to characterize the atmosphere during the testing.

In the illustrated embodiment, environment can be controlled at temperatures between minus 100° C. and plus 300° C.

In the illustrated embodiment, the system interfaces with existing dynamic testers such as MTS-880 or 831 type hydraulic testers. In the illustrated embodiment, the carousel is incorporated in an MTS dynamic tester and frame 62.

The invention also includes a method of automating the testing of samples. In the method, automating testing of a sample comprises the steps of (a) providing a carousel with multiple stations for holding samples to be tested; (b) designing sample holding means in the multiple stations to make possible the removal of a sample from the sample holding means using mechanical means to place the sample in position to be measured; and c) evaluating a sample by imaging means. In the method, a vacuum device can be used to withdraw a sample from the sample holding means and digital means can be used to view a sample and collect data on the sample.

What is claimed is:

1. An apparatus for automatically testing multiple samples comprising:
    (a) a carousel having a plurality of stations for holding samples to be tested;
    (b) sample holding means associated with said carousel, said sample holding mean being adapted to retain samples during static or dynamic testing of the samples and to release said samples when measurements are made;
    (c) a vacuum device associated with said carousel for removing a sample from sample holding means;
    (d) a measuring device associated with said carousel for evaluating a sample when a sample is withdrawn from the sample holding means by said vacuum device.

2. The apparatus of claim 1 wherein at least the carousel, the sample holding means and vacuum device are contained within an environmental chamber.

3. The apparatus of claim 2 wherein the measuring device is an imaging device outside the environmental chamber.

4. The apparatus of claim 1 wherein the carousel has an upper part and a lower part and the sample holding means has a first portion associated with the upper part of said carousel and a second portion associated with the lower part of said carousel, and the lower part and upper part of said carousel are moveable relative to one another.

5. The apparatus of claim 4 wherein the upper portion and the lower portion of the carousel are mounted on a spindle and have actuating means for advancing the carousel in increments corresponding to sample holding means in said carousel.

6. The apparatus of claim 4 wherein the upper portion and the lower portion of the carousel are actuated to move back and forth relative to each other while sample holding means in the upper portion and lower portion remain aligned.

7. The apparatus of claim 6 which is actuated ten times per second to provide dynamic flexing of rubber samples.

8. The apparatus of claim 2 in which said environmental chamber has means for controlling atmosphere and temperature.

9. The apparatus of claim 1 in which the measuring means is a digital imaging device.

10. A method for automatic testing of a sample comprising the steps of:
    (a) providing a carousel with multiple stations for holding samples to be tested;
    (b) retaining the samples within the carousel during static or dynamic testing of the samples;
    (c) releasing the samples when measurements are made;
    (d) withdrawing a sample from the carousel when measurements are made; and
    (e) measuring and evaluating the withdrawn sample by means of a measuring device.

11. The method of claim 10, wherein the sample is withdrawn from the carousel by means of a vacuum device associated with the carousel.

12. The method of claim 10, wherein the measuring device comprises an imaging device.

13. The method of claim 10 comprising the further step of enclosing the carousel in an environmental chamber.

14. The method of claim 13 comprising the further step of providing means for controlling the atmosphere within the environmental chamber.

15. The method of claim 10, wherein the retention of the samples within the carousel during static or dynamic testing of the samples and release of the samples when measurements are made is by means of sample holding means contained with the carousel within an environmental chamber.

* * * * *